United States Patent [19]
Giordano et al.

[11] Patent Number: 5,705,344
[45] Date of Patent: Jan. 6, 1998

[54] HIGH-THROUGHPUT SCREENING ASSAY FOR INHIBITORS OF NUCLEIC ACID HELICASES

[75] Inventors: Heidi Giordano, Oakland; Michael G. Peterson, Millbrae; Mohanram Sivaraja, Mountain View, all of Calif.

[73] Assignee: Tularik, Inc., South San Francisco, Calif.

[21] Appl. No.: 616,046

[22] Filed: Mar. 14, 1996

[51] Int. Cl.$^6$ ........................................... C12Q 1/68
[52] U.S. Cl. ........................... 435/6; 935/77; 935/78; 435/196
[58] Field of Search ............... 135/6, 196; 436/501; 935/77, 78

[56] References Cited

U.S. PATENT DOCUMENTS

| | | | |
|---|---|---|---|
| 4,203,848 | 5/1980 | Grandine, II | 210/490 |
| 5,217,864 | 6/1993 | Heintz et al. | 435/6 |
| 5,273,881 | 12/1993 | Sena et al. | 425/6 |
| 5,466,576 | 11/1995 | Schulz et al. | 435/6 |

OTHER PUBLICATIONS

Matson (1986) J. Biol. Chem. 261:10169–75.
Matson and Bean (1995) Methods Enzymol. 262:389–405.
Poll et al. (1994) Biochemistry 33:3841–47.
Crute et al. (1995) J. Med. Chem. 38:1820–25.
Sun and Hurley (1992) J. Med. Chem. 35:1773–82.
Amaratunga et al. (1993) Biochemistry 32:6815–20.
Matson and Kaiser–Rogers (1990) Annu. Rev. Biochem. 59:289–329.
Bachur et al. (1992) Mol. Pharm. 41:993–8.
Schaeffer et al. (1993) Science 260:58–63.
Tuteja et al. (1990) Nucl. Acids Res. 18:6785–92.
Tuteja et al. (1992) Nucl. Acids Res. 20:5329–37.
Maine et al. (1992) Biochemistry 31:3968–75.
Naegeli et al. (1993) Biochemistry 32:613–21.
Seki et al. (1990) Biochemistry 29:1003–9.

*Primary Examiner*—W. Gary Jones
*Assistant Examiner*—Amy Atzel
*Attorney, Agent, or Firm*—Richard Aron Osman

[57] ABSTRACT

The invention provides screening assays for identifying an inhibitor of a pathogenic helicase activity, e.g. a helicase derived from a pathogenic infectious organism such as a bacterium, protozoan or fungus. Helicase activity is detected by the solid-phase, preferential capture of retained (non-liberated) single-stranded nucleic acid comprising a detectable label.

17 Claims, 4 Drawing Sheets

UL5/52 Dose Response

M13 Template Dose Response

Effect of Temperature on UL5/52 Activity

Effect of pH on UL5/52 Activity

OBP Dose Response

M13 Dose Response

Effect of Temperature on OBP Activity

Effect of pH on OBP Activity

HIGH-THROUGHPUT SCREENING ASSAY FOR INHIBITORS OF NUCLEIC ACID HELICASES

INTRODUCTION

1. Field of the Invention

The field of this invention is assays for screening for inhibitors of a certain class of enzymes, namely nucleic acid helicases.

2. Background

Helicases are enzymes which unwind double-stranded nucleic acids, usually in an NTP-dependent manner. Cellular, microbial, phage, and viral helicases are involved in a wide variety of cellular functions including DNA replication, recombination, and repair and RNA transcription, translation, and processing. Because of the critical functions played by helicases, they provide promising targets for therapeutic intervention, e.g. in pathogenic infection. For example, many infectious diseases, especially fungal and viral disease, have resisted efforts to identify effective pharmaceutical therapies.

Identifying and developing new pharmaceuticals is a multibillion dollar industry in the U.S. alone. Especially needed are efficient methods of identifying pharmacological agents or drugs which are active against pathogens which have hitherto defied effective therapy. If amenable to automated, cost-effective, high throughput drug screening, assays for specific helicase inhibitors would have immediate application in a broad range of domestic and international pharmaceutical and biotechnology drug development programs.

The standard assay for measuring helicase activity uses gel electrophoresis to monitor unwinding of double-stranded DNA. Because this assay is time-consuming and cumbersome, several additional types of helicase assays have been developed: measuring the sensitization of labeled duplex DNA to single-strand specific nucleases, electron microscopy, displacement of a labeled fragment which is annealed to a single-stranded DNA or RNA molecule, and more recently, spectrophotometric assays utilizing a dye or ssDNA binding protein as the reporter molecule. Unfortunately, each of these assays has limitations which restrict their applicability to high-throughput drug screening: they are slow, expensive, insensitive, subject to interference and/or require considerable manipulation.

Relevant Literature

Matson et at. (1990) Annu Rev Biochem 59, 289–329 provides an overview of helicases and helicase assays.

Houston and Kodadek (1994) Proc Natl Acad Sci USA 91, 5471–6474 and Raney et al. (1994) Proc Nail Acad Sci USA 91, 6644–6648 describe spectophotometic helicase assays. Roman and Kowalczykowski (1989) Biochemistry 28, 2863–2873 describes a helicase assay exploiting the intrinsic fluorescence of E. coli SSB protein that is quenched when the protein binds single-stranded DNA.

SUMMARY OF THE INVENTION

The invention provides methods and compositions for detecting helicase activity and identifying modulators of pathogenic nucleic acid helicase activity. Helicase activity is detected by the solid-phase, preferential capture of retained (non-liberated) single-stranded nucleic acid comprising a detectable label. The invention includes methods of screening for helicase activity by comparing candidate helicase activities with one or more defined control helicase activities or screening for modulators of one or more defined helicase activities by comparing helicase activities in the presence and absence of a candidate modulator.

The general method for identifying modulators of helicase activity involves steps:

forming a mixture of a labeled first single-stranded nucleic acid comprising a label, an unlabeled second single-stranded nucleic acid, a pathogenic nucleic acid helicase, a nucleoside triphosphate, and a candidate agent, wherein the first and second nucleic acids are hybridized;

incubating the mixture in a reservoir under condition whereby, but for the presence of the candidate agent, the helicase unhybridizes the first and second nucleic acids at a first helicase activity;

immobilizing the second nucleic acid on a solid substrate;

separating any unhybridized first nucleic acid from the second nucleic acid to obtain isolated second nucleic acid;

measuring the mount of the label retained on the isolated second nucleic acid to obtain a second helicase activity;

wherein a difference between the first and second helicase activity indicates that the candidate agent modulates the activity of the pathogenic nucleic acid helicase.

In specific embodiments of the invention, the immobilizing step comprises directly or indirectly (e.g. through an avidin-biotin complex), noncovalently and preferentially binding the second nucleic acid to the solid substrate. For example, the solid substrate may be a glass bead and the preferential affinity resulting from the second nucleic acid being of greater length than the first nucleic acid.

The separating step may involve filtering the solid substrate through a specialized apparatus comprising a tube having a fluid passage comprising a reservoir portion and a evacuation portion, a filter extending transversely across the passage and separating the reservoir and evacuation portions, said filter being changeable from substantially water-impermeable to water-permeable, having a maximum pore size sufficiently large to freely pass said any unhybridized first nucleic acid and sufficiently small to retain said solid substrate; for example, by contacting the filter with an effective concentration of a "wetting agent" such as an organic solvent.

DETAILED DESCRIPTION OF THE INVENTION

Figure 1:
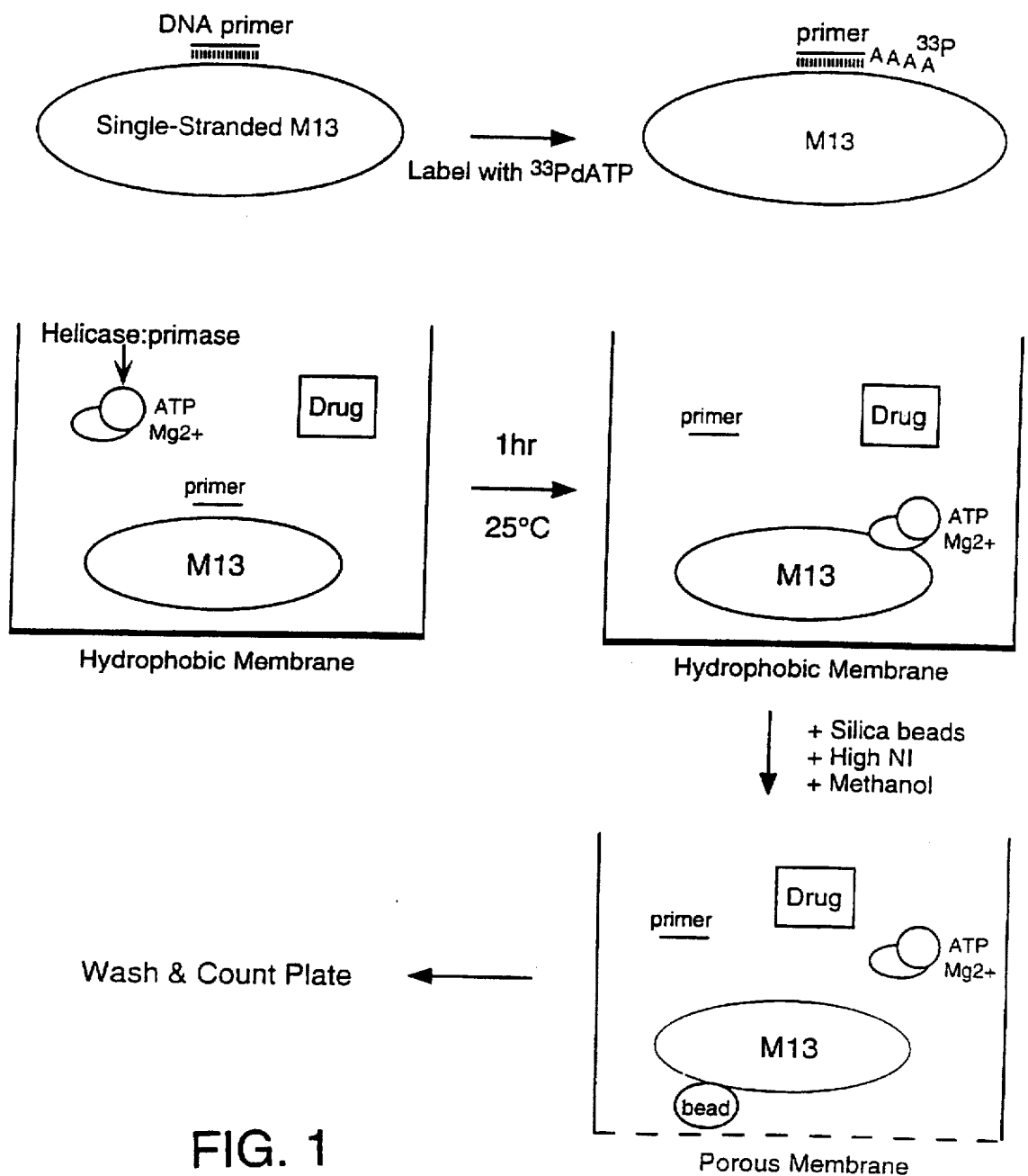
FIG. 1 shows a schematic of an automated Herpes Simplex Virus UL5/52 helicase assay.
Figure 2:
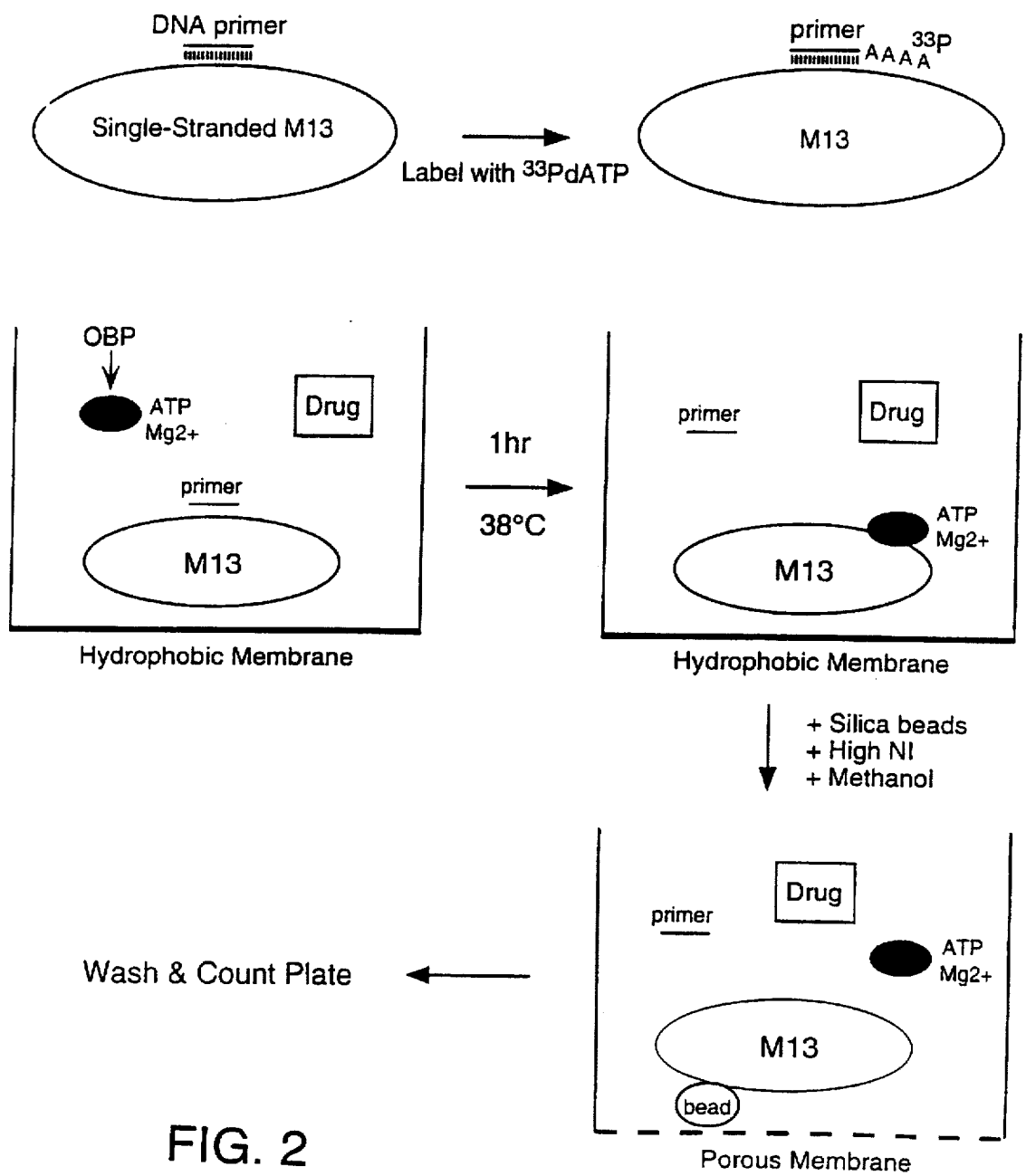
FIG. 2 shows a schematic of an automated Herpes Simplex Virus OBP helicase assay.
Figure 3A:
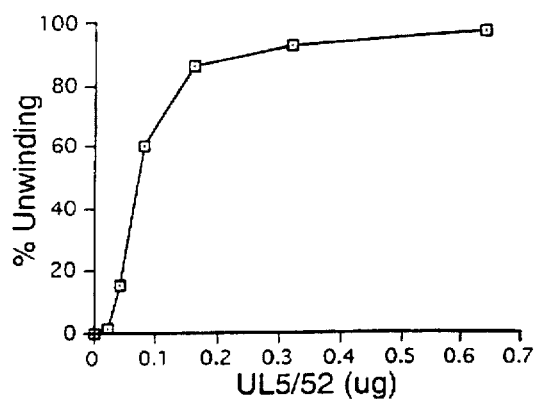
FIGS. 3A–3D provide a characterization of the Herpes Simplex Virus UL5/52 helicase assay.
Figure 3B:
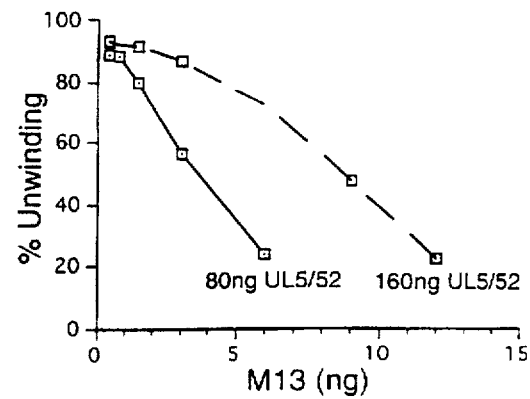
Figure 3C:
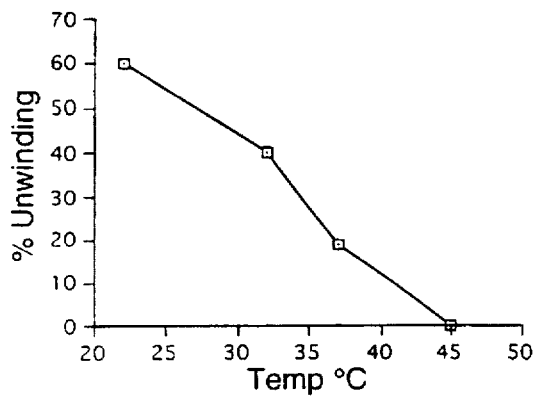
Figure 3D:
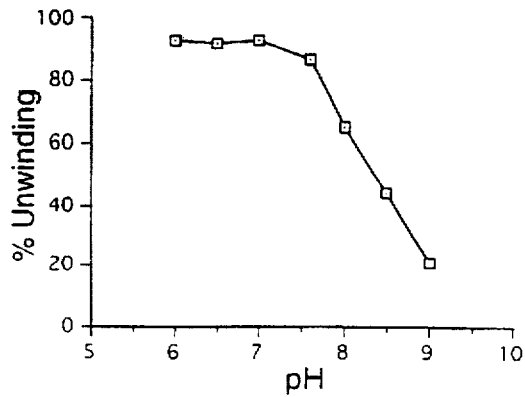
Figure 4A:
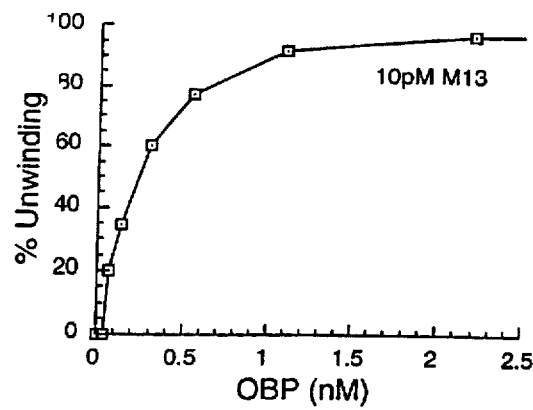
FIGS. 4A–4D provide a characterization of the Herpes Simplex Virus OBP helicase assay.
Figure 4B:
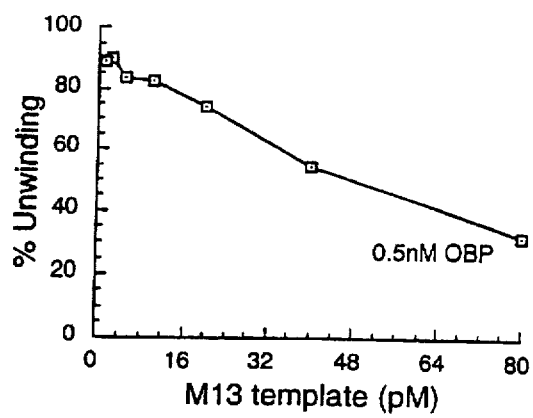
Figure 4C:
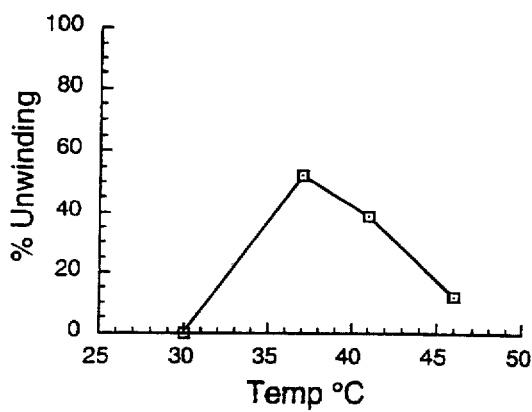
Figure 4D:
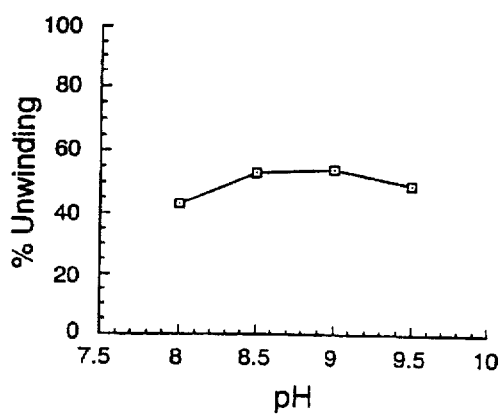

The invention provides efficient methods and compositions for detecting helicase activity and identifying specific modulators of nucleic acid helicase activity. The methods are amenable to automated, cost-effective high throughput drug screening and have immediate application in a broad range of domestic and international pharmaceutical and biotechnology drag development programs. In addition, the invention provides kits for helicase modulator screening which include premeasured amounts of the compositions used in the disclosed methods.

Since helicases are necessary for a wide variety of cellular functions including growth, target diseases are limited only in that disease or disease progression be subject to inhibition by modulation of the activity of one or more specific helicases. As such, target diseases include viral, bacterial and fungal infections, metabolic disease, genetic disease, cell growth and regulatory disfunction, such as neoplasia, inflammation, hypersensitivity, etc. The target diseases may be afflictions of plants, especially agricultural crops, or animals, especially livestock, house animals and humans.

The initial step of the general method involves forming a mixture of a labeled first single-stranded nucleic acid comprising a label, an unlabeled second single-stranded nucleic acid, a pathogenic nucleic acid hellcase, a nucleoside triphosphate, and a candidate agent wherein the first and second nucleic acids are hybridized.

The hybridized first and second nucleic acids may be RNA or DNA, linear or circular, depending on the specificity of the targeted helicase. In addition, other nucleic acids or structural analogs may be substituted so long as they provide an active substrate for the targeted helicase activity. The nucleic acids may be of any length amenable to the assay conditions and requirements. For example, ensuring helicase substrate specificity and minimizing non-specific renaturation requires a minimal region of complementarity between the first and second nucleic acids, typically at least about 12, more typically at least about 18 and preferably at least about 24 continuous base pairs. In one embodiment, the differential affinity of the nucleic acids for the solid substrate is a result of a size differential between the strands. In this case, the sizes are selected to maintain differential affinities sufficient to provide statistically significant assay results; frequently the sizes will differ by at least one or two orders of magnitude. In general, optimal lengths are readily determined empirically.

The nucleic acids may be of any sequence which provides a convenient substrate for the targeted helicase(s). The nucleic acids may be complementary over the entire length of at least one of the nucleic acids or there may be regions of noncomplementary 5' and/or 3' of the complementary region. Introducing these 5' and/or 3' noncomplementary regions provides molecular forks that yield better substrates for some helicases. Generally, conveniently replicated vectors e.g. phage, or restriction fragments thereof, provide an inexpensive source of the nucleic acids. The assays are generally compatible with the presence of DNA binding proteins, such as histories. It is often advantageous to include a variety of potential substrates, e.g. double-stranded nucleic acids of varied size, sequence, protein complexing, etc. to improve the likelihood of detecting substrate-sensitive helicases.

The first nucleic acid comprises a detectable label, which label is absent from the second nucleic acid. A wide variety of directly and/or indirectly detectable labels may be used so long as they are compatible with the assay. Exemplary directly detectable labels include radiolabels, fluorescent labels, etc.; exemplary indirectly detectable labels include epitope tags, biotin, nucleoside analogs such as digoxigenin, etc.

The pathogenic helicase (i.e. any helicase activity that is harmful or acting harmfully to the host cell or organism) is selected based on the target application. Rapidly growing cells (e.g. in neoplasia) may be targeted by inhibitors of human helicases, especially replicative helicases. In addition, pathogen-selective or -specific helicases are used to identify pharmacological therapeutics for the treatment of infectious disease. Fungal, viral, bacterial and parasitic helicases, in particular, provide medically urgent targets for identifying inhibitors by the subject methods. Alternatively, a plurality of helicases or panel comprising a preselected range of different helicases can be used to maximize the scope of the assay.

Preferred pathogenic helicases derive from medically significant infectious fungi such as *Aspergillus, Candida species;* bacteria such as *Staphylococci* (e.g *aureus*), *Streptococci* (e.g. *pneumoniae*), *Clostridia* (e.g. *perfringens*), *Neisseria* (e.g *gonorrhoeae*), *Enterobacteriaceae* (e.g. *coli*), *Helicobacter* (e.g *pylori*), *Vibrio* (e.g. *cholerae*), *Capylobacter* (e.g. *jejuni*), *Pseudomonas* (e.g *aeruginosa*), *Haemophilus* (e.g. *influenzae*), *Bordetella* (e.g. *pertussis*), *Mycoplasma* (e.g. *pneumoniae*), *Ureaplasma* (e.g. *urealyticum*), *Legionella* (e.g. *pneumophila*), *Spirochetes* (e.g. *Treponema, Leptospira and Borrelia*), *Mycobacteria* (e.g. *tuberculosis, smegmatis*), *Actinomycies* (e.g. *(israelii)*, *Nocardia* (e.g. *asteroides*), *Chlamydia* (e.g. *trachomatis*), Rickettsia, Coxiella, Ehrlichia, Rochalimaea, Brucella, Yersinia, Fracisella, and Pasteurella; protozoa such as sporozoa (e.g. Plasmodia), rhizopods (e.g. Entamoeba) and flagellates (Trypanosoma, Leishmania, Trichomonas Giardia, etc.); and viruses such as (+) RNA viruses (examples include Picornaviruses, e.g. polio; Togaviruses, e.g. rubella; Flavivimses, e.g. HCV; and Coronaviruses), (−) RNA viruses (examples include Rhabdoviruses, e.g. VSV; Paramyxovimses, e.g. RSV; Orthomyxovimses, e.g. influenza; Bunyaviruses and Arenaviruses), dsDNA viruses (Reoviruses, for example), RNA to DNA viruses, i.e. Retroviruses, e.g. HIV, and certain DNA to RNA viruses such as Hepatitis B virus.

The helicase may be purified from a natural soume or may be recombinant and is usually provided in at least a partially-purified form. Often only a portion of the native helicase is used in the assay, the portion being sufficient for helicase activity, preferably not less than an order of magnitude less than that of the full-length helicase. Portions capable of imparting the requisite binding specificity and affinity are readily identified by those skilled in the art. A wide variety of molecular and biochemical methods are available for generating catalytic portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art.

The reaction mixture also comprises a candidate agent such as a preselected candidate helicase inhibitor or, especially for high-throughput drug screening, a library-derived candidate agent. Library-derived candidate agents encompass numerous chemical classes, though typically they are organic compounds; preferably small organic compounds. The libraries may comprise synthetic and/or naturally derived compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs. The agent is provided in standard serial dilutions or in an amount determined by analogy to known modulators.

In addition, the mixture usually includes additional reagents, such as salts, buffers, etc. to facilitate or maximize helicase activity. Also, reagents that reduce non-specific or background denaturation or otherwise improve the efficiency of the assay, such as protease inhibitors, nuclease inhibitors, antimicrobial agents, single-stranded DNA binding protein, etc. may be used.

The second step of the general method involves incubating the mixture in a reservoir under conditions whereby, but for the presence of the candidate agent, the helicase (or helicases) unhybridizes the first and second nucleic acids at a first, control helicase activity and so converts at least a detectable portion, and preferably, substantially all of the initial amount of double-stranded nucleic acid into unhybridized complementary single-stranded nucleic acid, whereby a final amount of the double-stranded nucleic acid remains (i.e. results or is formed). As such, depending on the stop point of the reaction, the measured activity may reflect a catalytic rate or an equilibrium constant. A wide variety of reaction conditions can be employed depending on the targeted helicase(s); in vitro conditions to support activity of exemplary helicases are exemplified below and/or otherwise known in the art. For example, the reaction generally requires the presence of an effective amount of a nucleoside triphosphate, such as ATP. For many helicases pathogenic in mammals, the reaction is carried out at room or elevated temperatures, usually in the range of 20° to 40° C., conveniently at room (ca. 25° C.) temperature. For high-throughput applications, reactions time is minimized, and is usually from 0.1 to 4 hours, more usually about 0.5 to 1.5 hours.

Following incubation, the second nucleic acid is preferentially immobilized on a solid substrate, i.e. the second nucleic acid has a higher affinity for the substrate than does the first. Preferred solid substrates for this capture step maximize the disparity in binding affinities and second nucleic acid binding affinity and binding sites, and hence, maximize signal strength and the signal-to-noise ratio. The affinity for the second nucleic acid may be direct (substrate-nucleic acid), indirect via a ligand (substrate-ligand-nucleic acid) or ligand receptor complex (substrate-receptor-ligand-nucleic acid), etc. As examples: silica-based bead substrates may be used to size-select the nucleic acids directly; magnetized substrates may be used to distinguish second nucleic acid comprising an iron-based ligand; substrates comprising a surface bound antibody receptor may be used to distinguish second nucleic acid comprising a specific ligand antigen of the antibody receptor; etc. To avoid interference, any selected ligand should not be identical to any selected label or label component.

In another embodiment, the hybridized nucleic acids are preferentially immobilized on the solid substrate, i.e. the hybridized nucleic acids have a higher affinity for the substrate than does at least the first nucleic acid, and frequently, both first and second nucleic acids. In this embodiment, the substrate frequently distinguishes double-stranded from single stranded nucleic acid based on differential net charge or charge distribution. An exemplary solid substrate useful in this embodiment is crystalline hydroxyapatite.

Preferred substrate structures includes fine fibers, beads, etc., and in particular, polymeric or silica-based microbeads of size, range and structure to maximize surface area, filter retention and bead suspension time during the assay incubations. Generally, such bead diameters range from 1 to 400 um, usually from 2 to 200 um. Depending on the selected capture mechanism, the mixture may be supplemented with a suitable pH buffer and salt to ensure the ionic strength and pH of the mixture is conducive to optimal binding. For high-throughput applications, the capture incubation is generally less than 4 hours, preferably less than 2 hours, more preferably less than about 1 hour. Typically, capture is most conveniently done at room temperature.

Following immobilization, the solid substrate is washed free of unhybridized first nucleic acid. The method used for separating and washing depends on the nature of the reaction reservoir and the solid substrate. For example, where the substrate is in the form of aggregated fibers, the solid phase may be physically transferred from the reaction reservoir to a series of rinse reservoirs. In a preferred embodiment, the separating and washing steps are performed by filtration, frequently vacuum-assisted filtration. In a particular embodiment, the method uses a filter that is changeable from water-impermeable to water-permeable having a maximum pore size sufficiently small to retain the selected solid substrate, e.g. a maximum pore size less than about 200 um diameter is typically used retain microbeads, by "wetting" the filter, e.g. contacting the filter with an effective concentration of an organic solvent, optionally supplemented with an effective amount of a detergent such as NP-40. In this specific embodiment, typical organic solvents include alcohol, conveniently methanol, solutions in the 5 to 90% range, conveniently about 10% (v/v). The filter should minimize final retention of unhybridized and immobilized labeled first nucleic acid under the assay conditions. A particular embodiment uses a GF/C hydrophobic glass fiber membrane (Polyfiltronics, Rockland, Mass.), or alternatively, a GF/C hydrophilic glass fiber membrane (Polyfiltronics, Rockland, Mass.) superimposed with an MP PP hydrophobic polypropylene membrane (Polyfiltronics, Rockland, Mass).

After washing, the amount of label retained on the substrate is measured to infer the helicase activity in the presence of the candidate agent, wherein a difference between the activity in the presence and absence of the agent indicates that said candidate agent modulates the activity of the targeted helicase. A variety of methods may be used to detect the substrate-bound label depending on the nature of the label and other assay components. Labels may be directly detected through optical or electron density, radiative emissions, nonradiative energy transfers, etc. In the preferred case of radioactive labels, emissions may be detected directly, e.g. with particle counters or indirectly, e.g. with scintillation cocktails and counters. In a specific embodiment, the bottom of the filtration tube is heat-melt sealed by contacting the tube-bottom with a hot plate, scintillation cocktail is added to the reservoir, and the radiolabel present in the tube counted.

The disclosed methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive enzymes, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In a particular embodiment, the robotic arm is equipped with a general purpose retrieving hand and a pipetting hand. The pipetting hand equipped with a multichannel pipettor retrieves and transfers measured aliquots of each an assay buffer, a solution comprising one or more candidate agents, a solution comprising a labeled oligonucleotide hybridized to a plasmid or viral template, and a solution comprising the targeted helicase activity into each designated filtration well of a microtiter plate, wherein each well comprises an upper reservoir portion with a bottom made of a solvent-permeablizing membrane. The general purpose hand then transfers each microtiter plate to an incubator. After a first incubation period for a time and at a temperature to permit assay-detectable unwinding (e.g. 0.5 to 1.5 hours at 38° C.), the general purpose hand transfers each plate to a microbead dispensing station (e.g. a Multidrop system) which deposits in each designated well a measured aliquot of a slurry of GLASSFOG® (BIO 101, tel: (800)424-6101) microbeads and a solution of an organic solvent (e.g. methanol) at a concentration sufficient to permeablize the filter to water (e.g. about 12.5% v/v, final concentration), yet retain the beads. After a second incubation period for a time and at a temperature to permit assay-detectable immobilization (e.g. 0.5 to 1.5 hours at room temperature), the general purpose hand transfers each plate to a vacuum diaphragm where the substantially all of the liquid phase is simultaneously filtered from each well. A measured aiquot of wash solution is then added and then vacuum filtered through each well until background counts are reduced to an assay-acceptable level. Optionally, the bottom of each plate may be blotted onto an absorbent membrane after one or more filtration steps to remove residual liquid from the bottom of each well. The bottom of the drip director of each well is then sealed (e.g. heat melt sealed) and a measured aliquot of scintillation cocktail added to each well. Thereafter, the mount of label retained in each designated well is quantified.

Assays for helicase activity per se are carried out substantially as described above except for the omission of the candidate agent. Furthermore, candidate helicase activity samples are compared with one or more known helicase activities, preferably a panel of defined activities. The candidate helicase samples are typically cellular or nuclear extracts.

In a preferred embodiment, the panel of control helicases comprises a range of different activities to maximize the likelihood of encompassing an activity functionally similar, in terms of the subject assay, to that sought to be detected in the sample.

The following examples are offered by way of illustration and not by way of limitation.

EXAMPLES

Example 1.

Preparation of Labeled M13 Substrate

Annealing Reaction

| | |
|---|---|
| 500 ul | M13mp18 ssDNA (500 ug, 250 pmoles total) |
| 6.4 ul | M13-complementary 22-mer oligonucleotide primer (1 ug/ul, 1000 pmoles total) |
| 140 ul | 10X Annealing Buffer (500 mM NaCl, 200 mM MgCl$_2$ and 400 mM TRIS ™-Cl, pH 7.5) |
| 53.6 ul | ddH$_2$O |
| 700 ul | Total |

70 C., 10 min., then 55 C., 1 hr. Store at −20 C. until further use.

Labeling Reaction

| | |
|---|---|
| 175 ul | Annealing reaction (125 ug total) |
| 3.0 ul | 0.5M DTT (5 mM final) |
| 100 ul | $^{33}$P-dATP (2000 Ci/mmol, 1 mCi total, 500 pmol total) |
| 24 ul | Klenow fragment (5 Units/ul) |
| 302 ul | Total |

Mix by gentle vortex, then buzz in microfuge to bring to bottom. Incubate at 25° C. (room temperature) for 45 min.

QUICKSPIN™ Column Preparation

At 30 min. into the labeling reaction, remove 2 Large Scale QUICKSPIN™ columns (3.0 ml bed volume). Invert several times to mix resin, then remove top cap, followed by bottom cap. Place column in collection tube and spin at 2,000 rpm for 4 min. Remove supernatant from collection tube and spin again at 2,000 rpm for 4 min. Replace the collection tube with an EPPENDORF™ tube and store upright until ready to use.

Removal of Klenow and Unicorporated Nucleotide

Add 300 ul Phenol/Chloroform/Isoamyl alcohol (50:49:1). Vortex briefly, then spin in microfuge 2 minutes. Carefully remove as much of the upper aqueous phase as possible without disturbing interface. Transfer aqueous phase to QUICKSPIN™ column that has been "spun dry." Spin at 2,000 rpm for 6 minutes. Collect supernatant (take note of volume) and transfer to another QUICKSPIN™ column and spin at 2,000 rpm for 6 minutes. Remove supernatant to sterile 1.5 ml EPPENDORF™ tube. Take accurate volume measurement.

Example 2.

HSV Helicase/Primase Manual Assay Protocol

Final Conditions

Reaction is done on a polypropylene 96 well plate. The total reaction volume is 100 μL. Add assay buffer 20 mM HEPES™ (pH 7.6) 4 mM MgCl$_2$ 4 mM ATP 100 μg/ml BSA 5% glycerol 2 mM DTT Add 10% DMSO. Add UL5/52 Helicase. Add $^{33}$P dATP labeled oligo annealed on the M13 template. Incubate for 1 hr at 25° C. Add 2× capture buffer containing silica beads.

25% MeOH 3.0M NaI 0.3% RIP-40™ 10% GLASS-FOG® beads

Incubate for 30 min. at 25° C. Transfer to GF/C Unifilter hydrophilic plate using cell harvester Wash five times with wash buffer 50% EtOH 0.2% RIP-40™ 50 mM NaCl 1 mM EDTA Count Seal plates using hot plate. Add 160 ul of scintillation cocktail. Seal bottom and top with Packard plate sealer. Count in Topcount scintillation counter.

Example 3.

HSV OBP Automated Helicase Assay Protocol
1. 1× Helicase Assay Buffer from 5× Stock Assay Buffer
5× stock Helicase assay buffer

| Concentration | 100 ml |
|---|---|
| 20 mM CHES ™ | 10 ml 1M (pH 9, KOH)(Sigma cat # C2885) |
| 8 mM MgCl | 4 ml of 1M |
| 500 ug/ml BSA | 250 mg |
| 3% Glycerol | 15 ml |
| | Add ddH2O to 100 ml |

To make 500 ml of 1× helicase assay buffer add fresh daily:

| Concentration | |
|---|---|
| 5x helicase buffer | 100 ml 5x buffer |
| 2.5 mM DTT (to final conc.) | 250 ul of 5M |
| 8 mM ATP (to final conc.) | 2.2 g |
| | Add ddH$_2$O to 500 ml | pH the 1x buffer to pH 9.0 using 10 N NaOH 2. 5× Substrate/Enzyme Buffer (SEB) Add Fresh Daily

| Concentration | 100 ml |
|---|---|
| 20 mM CHES ™ | 10 ml 1M |
| 500 ug/ml BSA | 250 mg |
| 3% Glycerol | 15 ml |
| 100 mM KCl | 16.5 ml 3M |

To make 1× add fresh daily:

| | 100 ml |
|---|---|
| 5 x SEB | 20 ml |
| 2.5 mM DTT | 50 ul 5M |
| | Add ddH$_2$O to 100 ml | pH the 1x buffer to pH 9.0 using 10 N NaOH

3. Wash Buffer

| Concentration | |
|---|---|
| 50% EtOH | 2 L (RICCA ™ from Baxter cat. # 65915) |
| 1 mM EDTA | 8 ml 0.5M |
| 0.2% np-40 ™ | 8 ml (Calbiochem cat. # 492015) |
| 50 mM NaCl | 40 ml 5M |
| | Add 4 L with ddH2O |

4. GLASSFOG® Silica Beads

| Concentration | 1 L |
|---|---|
| 25% MeOH | 250 ml (Fisher cat. # A452-4) |
| 3M NaI | 500 ml 6M (BIO 101 cat. # 1001-801) |
| 0.3% np-40 ™ | 3 ml |
| 10% BIOBEADS | 100 ml (BIO 101 cat. # 1005-904) |
| | Bring up to 1 L with dd H2O |

5. M13/Enzyme Mixture

M13 fixed at 2.7 ng/well Stock M13 is 380 ng/ul (Apr. 26, 1995) in TE OBP fixed at 4.0 ng/well Stock OBP is 1000 ng/ul (Apr. 17, 1995) in storage buffer (20 mM Hepes, pH7.9, 1M KCl, 15% Glycerol, 1 mM EDTA, 1 mM DTT, 1 mM NaMetabisulfate, 1 mM AEBSF (4-2-aminoethyl 7-benzenesulfyl fluoride hydorchloride Preparation of M13 Solution Volume needed for M13/OBP mixture (V)=# of plates×1 ml+12 ml Amount of M13 stock to be dissolved in V ml of SEB, (A) Multiply .27 ng/ul by the total volume needed and divide by stock concentration of M13.

Ex. V = 48 X 1 ml + 12 ml = 60 ml
Stock M13 conc. = 380 ng/ul
A = (.27 × 60,000 ul)/380 =
42.6 ul of stock M13 into 60 ml of SEB Preparation of OBP Solution Volume needed for M13/OBP mixture (V)=# of plates×1 ml+12 ml Amount of OBP stock to be dissolved in V ml of SEB, (B) Multiply 0.4 ng/ul by the total volume needed and divide by stock concentration of OBP.

Ex. V = 48 X 1 ml + 12 ml = 60 ml
Stock OBP conc. = 1000 ng/ul
B = (.45 × 60,000 ul)/1000
= 27 ul of stock OBP into 60 ml of SEB 6. Robotic Steps on ZYMARK™ Workstation T2

Add 15 ul 3M KCl to first column of hydrophobic GF/C plates (control for total binding of M13 template under conditions which inactivate OBP ie. high salt).

Add 80 ul of helicase buffer/well. Add 10 ul of compound/well. Add 10 ul of labeled substrate and enzyme in SEB/well. Shake 10 min. Place plates in incubator for 1 hr. at 38° C. Remove plates from incubator and add 100 ul of GLASS-FOG® beads. Sit for 30 minutes at 25° C. Wash plates with wash buffer.

7. Sealing and Counting of Plates

Seal plates using hot plate. Add 160 ul of scintillation cocktail. Seal bottom and top with PACKARD plate sealer. Count in TOPCOUNT scintillation counter.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying an agent that modulates the activity of a helicase comprising the following steps in consecutive order:
   a) forming a mixture of a labeled first nucleic acid hybridized to a complementary unlabeled second nucleic acid, a helicase, a nucleoside triphosphate, and a candidate agent, wherein said first and second nucleic acids are both DNA or are both RNA;

b) incubating said mixture in a reservoir under conditions wherein said helicase would unhybridize said first and second nucleic acids in the absence of said agent;

c) immobilizing said second nucleic acid on a solid substrate by direct noncovalent binding, wherein said second nucleic acid has a greater affinity for said solid substrate than does the first nucleic acid;

d) separating any unhybridized labeled first nucleic acids to obtain isolated, immobilized second nucleic acids;

e) measuring the amount of said label retained on the immobilized second nucleic acid, wherein the amount of said label is indicative of the modulation of helicase activity by said agent.

2. The method of claim 1, wherein said solid substrate is a micro-bead and said greater affinity results from said second nucleic acid being of greater length than said first nucleic acid.

3. The method of claim 1, wherein said second nucleic acid comprises a ligand, wherein said greater affinity results from said ligand having a greater affinity for said solid substrate than does said first nucleic acid.

4. The method of claim 3, wherein said solid substrate is coated with avidin, said ligand is biotin and said label is other than biotin.

5. The method of claim 3, wherein said solid substrate is coated with a digoxigenin-specific antibody, said ligand is digoxigenin and said label is other than digoxigenin.

6. The method of claim 1, wherein said label is a radiolabel.

7. The method of claim 1, wherein said label is a fluorescent label.

8. The method of claim 3, wherein said label is biotin and said ligand is other than biotin.

9. The method of claim 3, wherein said label is digoxigenin and said ligand is other than digoxigenin.

10. The method of claim 1, wherein said separating step comprises filtering said solid substrate.

11. The method of claim 1, wherein said separating step is performed in a tube having a fluid passage comprising a reservoir portion and a evacuation portion a filter extending transversely across said passage and separating said reservoir portion from said evacuation portion, said filter being changeable from water-impermeable to water-permeable having a maximam pore size sufficiently large to freely pass said any unhybridized first nucleic acid and sufficiently small to retain said solid substrate.

12. The method of claim 10, wherein said filter comprises a first membrane being changeable from water-impermeable to water-permeable by contacting said first membrane with an effective concentration of an organic solvent and a second membrane being water-permeable and having a maximam pore size less than about 200 um diameter.

13. The method of claim 1, wherein said helicase is a pathogenic helicase.

14. The method of claim 1, wherein said hellcase is a pathogenic fungal helicase.

15. The method of claim 1, wherein said helicase is a pathogenic human helicase.

16. The method of claim 1, wherein said helicase is a pathogenic bacterial helicase.

17. The method of claim 1, wherein said helicase is a pathogenic viral helicase.

* * * * *